United States Patent [19]

Fink

[11] Patent Number: 4,817,445
[45] Date of Patent: Apr. 4, 1989

[54] DEVICE FOR THE REMOVAL OF LIQUID SAMPLES

[75] Inventor: Willi Fink, Tübingen-Weilheim, Fed. Rep. of Germany

[73] Assignee: Edmund Bühler GmbH & Co., Tübingen-Weilheim, Fed. Rep. of Germany

[21] Appl. No.: 19,526

[22] Filed: Feb. 26, 1987

[51] Int. Cl.$^4$ .............................................. G01N 1/14
[52] U.S. Cl. ................................ 73/864.62; 73/864.63
[58] Field of Search ........... 73/863.01, 863.02, 863.03, 73/863.83, 863.84, 864, 864.01, 864.11, 864.13, 864.14, 864.15, 864.16, 864.17, 864.18, 864.21, 864.24, 864.34, 864.35, 864.61, 864.62, 864.63, 864.91

[56] References Cited

U.S. PATENT DOCUMENTS

| | | | |
|---|---|---|---|
| 2,260,419 | 10/1941 | Wrightsman | 73/864.62 |
| 3,892,130 | 7/1975 | Winget et al. | 73/864.62 |
| 3,990,312 | 11/1976 | Koukol | 73/864.15 |
| 4,028,750 | 12/1986 | Welker | 73/864.62 |
| 4,406,171 | 9/1983 | Veberschaer | 73/864.62 |
| 4,429,583 | 2/1984 | Watanabe et al. | 73/864.17 |
| 4,441,374 | 4/1984 | Suzuki | 73/864.21 |
| 4,557,151 | 12/1985 | Welker | 73/864.84 |
| 4,615,468 | 10/1986 | Gay | 73/864.91 |

FOREIGN PATENT DOCUMENTS 0239388 9/1925 United Kingdom ............ 73/864.16

Primary Examiner—Stewart J. Levy
Assistant Examiner—Robert R. Raevis
Attorney, Agent, or Firm—Michael J. Striker

[57] ABSTRACT

A device for the removal of liquid samples from a liquid receptacle comprises a sample container with a piston which subdivides the container into a first chamber receiving a liquid sample and a second chamber receiving a piston driving medium. The device further includes a dosing device for the piston driving medium, which is connectable to the sample container by a plug-in coupling which can be locked at both sides thereof.

8 Claims, 2 Drawing Sheets

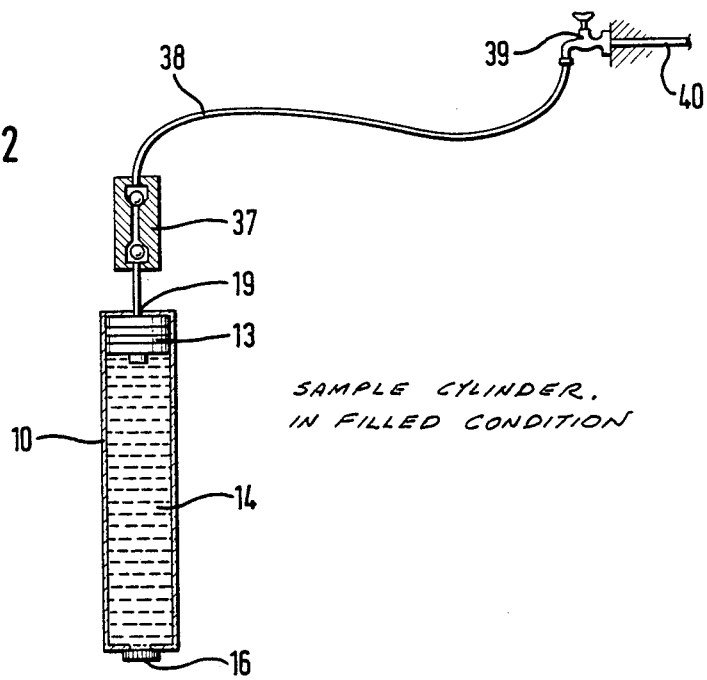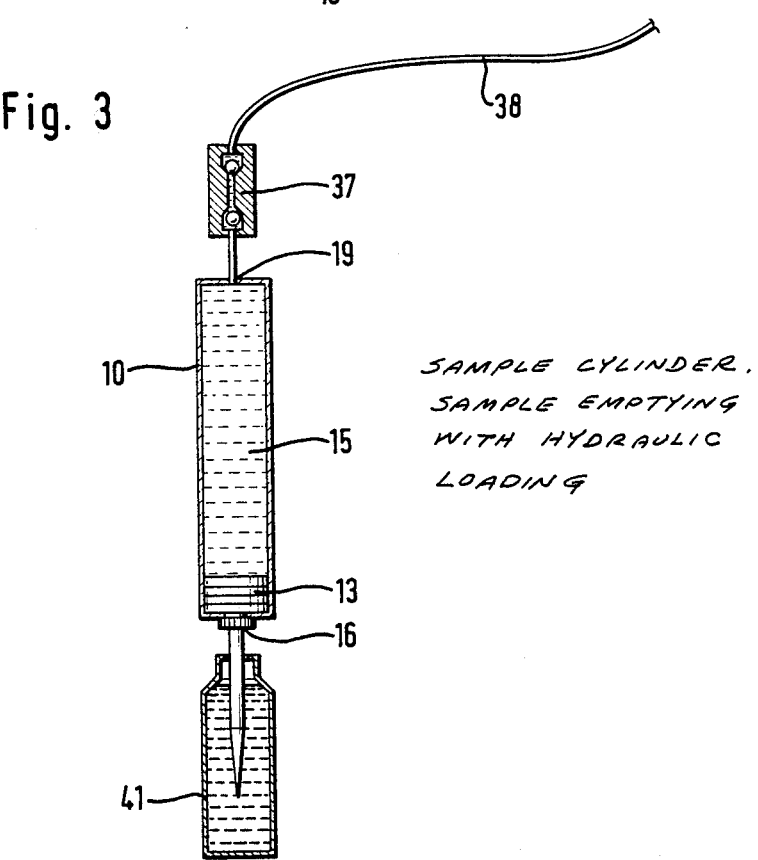

DEVICE FOR THE REMOVAL OF LIQUID SAMPLES

BACKGROUND OF THE INVENTION

The present invention relates to a device for the removal of liquid samples from natural or artificial collecting or flow-type liquid receptacles.

Sample-removing devices of the type under consideration have been known. Such devices comprise a cylindrical sample container subdivided by a freely movable piston into two cylindrical chambers, of which one has an opening for a sample liquid and the other has an opening for a piston-driving medium.

Known sample removing devices have been utilized for automatically taking samples from clean waters and waste waters. Water samples have been fed into a sample container. The sample removal has been carried out as a whole with the aid of liquid-conveying installations, specifically pressure or suction pumps. However, for the removal of liquid samples with very light volatile materials, for example chlorinated or halogenated carbon oxides, these known sample-removing devices can not be utilized because it can not be ensured with conventional devices that samples are removed under a complete air shutting-off, and in order to prevent strong overpressure or strong under-pressure from failing during the sample removal the volatilization of these materials from the liquid samples should be facilitated.

Also, often at the place of the sample removal and upon the occurence of dangerous materials, accident preventing direction diagrams can be noticed, which can not be obtained with conventional sample removing devices.

SUMMARY OF THE INVENTION

It is an object of the present invention to provide an improved device for the removal of liquid samples.

It is another object of the invention to provide a device with which the sample removal could be undertaken with a complete shut-off the air, and with a further avoidance of pressure loading of the liquid sample.

Yet another object of the invention is to provide a sample removal device which would enable the transport of the sample to the site of the sample analysis with a complete air shut-off and with the avoidance of pressure loading on the sample being transported.

These and other objects of the invention are attained by a device for the removal of liquid samples from natural or artificial liquid collecting or flow receptacles, comprising a cylindrical container, a piston freely movable in said container and subdividing said container into two cylindrical chambers, one of said chambers having a first opening for a sample liquid and another of said chambers having a second opening for a piston-driving medium, said first opening being immediately a sample liquid inlet to obtain a sample removal under air shut-off, said piston being leakage-free guided in said container and being closely before said first opening adjustable up to an initial position thereof; and a plug-in coupling connected to said second opening for connection with the piston-driving medium and being lockable at two sides thereof and leakage-free, said container constituting also a liquid sample transport container.

The first opening may be provided with a check valve.

With the device according to the invention an automatic liquid specimen removal with a complete air shut-off can be obtained at any chosen depth from the liquid receptacle. The removed liquid sample remains in the same vessel until the sample analysis so that the sample container which can be produced from a neutral material be not influenced by the sample.

The device may further include dosing means for the piston-driving medium, said dosing means including a dosing pump cylinder, a pump piston and a restoring spring, said pump piston being movable in said cylinder against said restoring spring to a predetermined position; a storage container for the piston-driving medium; a first valve interconnected between said plug-in coupling and said dosing pump cylinder; and a second valve interconnected between said storage container and said dosing pump cylinder so said dosing pump cylinder receiving the piston-driving medium is connected to said plug-in coupling via said first valve and to said storage container via said second valve, said first and second valve being adjustable and switchable in two opposite flow directions.

Due to the provision of the leakage-free plug-in coupling, a safe and simple handling of the device during the exchange of the sample container is ensured. Sample containers are easy to make and to clean. The entire device is mobile and can be installed at any chosen place.

The pump piston may be mechanically movable.

The dosing pump cylinder may be hydraulically actuated, the device may further include a control valve and a control medium pressure source, said dosing pump cylinder being connected to said pressure source by said control valve.

The dosing means may further include an adjustable or interchangeable stop, said pump piston being, under prestressing of said restoring spring, adjustable by said stop to an initial position thereof.

The control valve, the storage container and the pressure source may be installed in an operation and control part, said sample container and said dosing means being separated from said operation and control part.

The sample container with structural components thereof operating in contact with a sample material may be made of a material which is inert to said sample material.

The objects of the invention are further attained by a method for the removal of liquid samples from natural or artificial liquid collecting or flow receptacles by means of a cylindrical container having a freely movable piston subdividing said container into a first chamber receiving a sample liquid and a second chamber for a piston driving medium and connected to a dosing means provided with a pump piston movable in a dosing pump cylinder connected to a storage container by a lockable valve, the method comprising the steps of displacing the piston-driving medium by returning said pump piston during operation of said dosing means from a predetermined end position, from said second chamber into said pump cylinder when said lockable valve is locked so that said movable piston is moved into said second chamber and allows an amount of sample liquid corresponding to an amount of said displaced medium to flow into said first chamber without any air contact.

The hydraulic or pneumatic operating system, with the aid of the dosing means, can be formed so that it can operate at any location without electrically-conductive or electric structural components, and thus accidents in explosion-dangerous zones would not occur.

The pump piston can be movable not only mechanically but also pneumatically or hydraulically. With the hydraulic actuation of this piston, the dosing pump cylinder with its cylindrical chamber is connectable to the control medium pressure source via the control valve whereby various combinations of the piston-driving medium and control medium are possible. Gases can be utilized as a piston-driving medium and as a control medium.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWINGS

FIG. 2 shows a sample container in the filled condition before emptying; and

FIG. 3 shows the sample container after emptying.

DETAILED DESCRIPTION OF THE PREFERRED EMBODIMENTS

Figure 1:
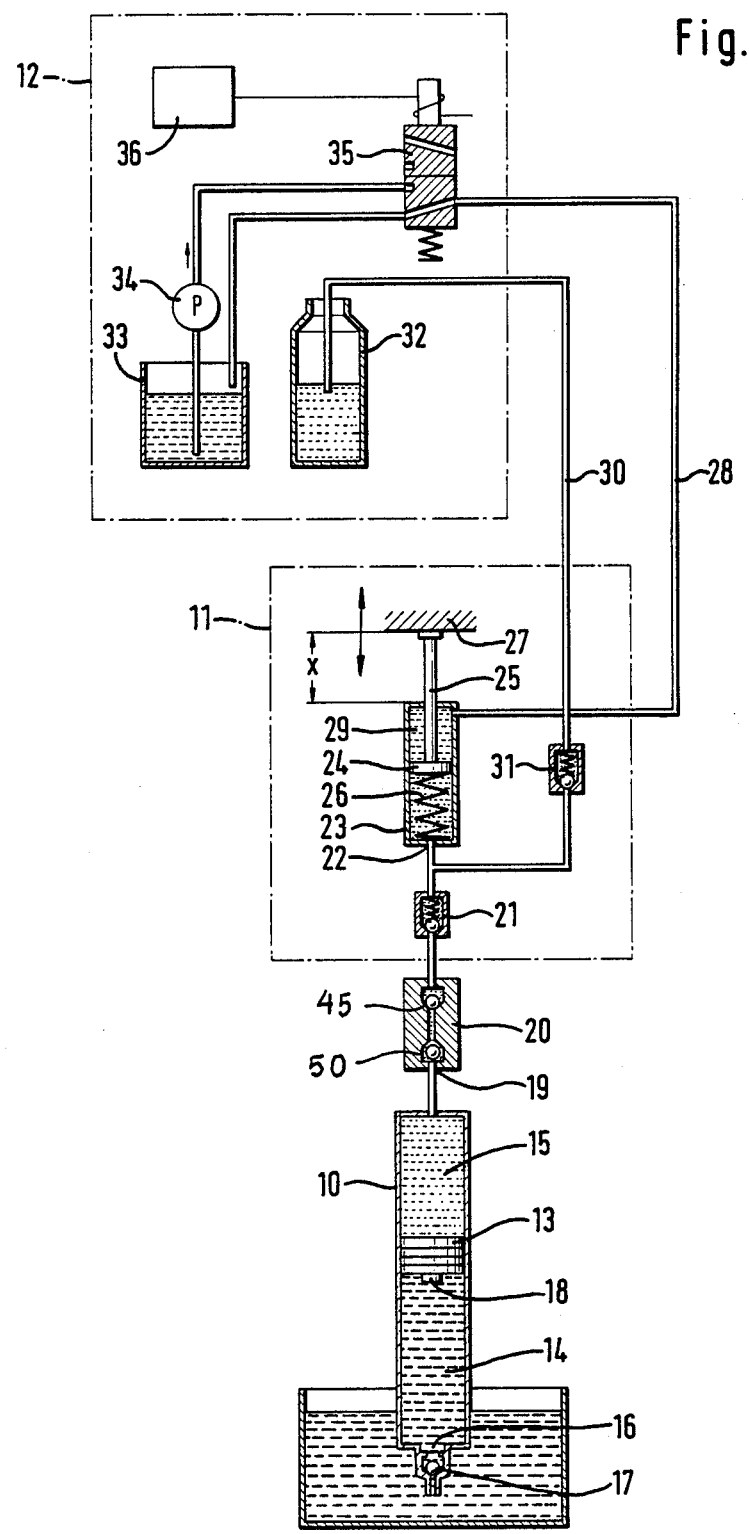
FIG. 1 is a schematic view of the device for taking liquid samples according to the invention.

Referring now to the drawings in detail, FIG. 1 illustrates the device of the invention which comprises three main parts, namely a sample container 10, a dosing device 11 and an operation and control device 12. The sample container 10 is made of solution-resistant and diffusion-resistant material and may be, for example, a glass cylinder. Sample container 10 has a piston 13 which has no piston rod and is freely movable and sealed against the wall of the sample container 10. Piston 13 subdivides the interior of container 10 into two different chambers 14 and 15. Chamber 14 serves for admitting a liquid sample and has at the end of container 10 an opening 16 which is provided in the exemplified embodiment with a check valve 17. Piston 13 at the side thereof, which faces the cylindrical chamber 14, has an abutment or projection 18 which is dimensioned so that it extends into the opening 16 up to the check valve 17 when piston 13 is in its initial position at the lower end of sample container 10. In this initial position, cheer 14 totally disasters and the respects container space is completely and practically air-free filled with piston 13.

The second cylinder chamber 15 is defined for admitting a hydraulic medium for driving the piston 13. This chamber 15 has, opposite to opening 16, a further opening 19 arranged in the container 10. This, opening is formed as a connection for a schematically shown plug in coupling 20 which is lockable at two sides by means of check valves 45 and 50 and is leakage-free. This plug-in coupling 20 is connected via a one-way valve 21 with an opening 22 of a dosing pump cylinder 23 of the dosing device 11.

The dosing pump cylinder 23 has a piston 24 with a piston rod 25 extending outwardly of the cylinder 23. Piston 24 is adjustable against the force of a return compression spring 66 in the dosing pump cylinder 23. The end of the piston rod 25 is positioned at an adjustable stop or abutment 27 by means of which the initial position of piston 24 and the prestressing of the adjusting spring 26 are influenced. The movement of piston 24 against the force of spring 26 is performed by means of a hydraulic control medium which flows from the operation and control device 12 via a line 28 into a chamber 29 of the dosing pump cylinder 23. A second hydraulic connection line 30 leads from the operation and control device 12, which, in case of explosion-resistant devices, can be detachable, via a one-way valve 31 to the opening 22 of the dosing pump cylinder 23. Both one-way valves 21 and 31 in the region of dosing device 11 are formed so that they lock the flow of the medium in two opposite directions.

The operation and control device 12 includes in the exemplified embodiment, a storage container 32 for the piston driving medium, a storage container 33 for a control medium, a pump 34 for pumping the control medium, and a switchable multi-way valve 35 arranged between the connection line 28 and the pump 34. Operation and control device 12 further includes a schematically shown control circuit 36, by means of which the operation of pump 34 for an automatic, for example time-dependent controlled sample removal, and the multi-way valve 35 are controlled in a known fashion.

FIG. 2 shows the sample container 10, the cylindrical chamber 14 of which is filled with a liquid sample admitted into chamber 14 through opening 16 with the air shut-off. Thereby the freely movable piston 13 is positioned, for example at the upper end of the sample container 10. The filled sample container 10 detached from the plug-in coupling 20 is, at the place of the sample analysis, connected to one side of the two-side lockable and leakage-free plug-in coupling 37 which is connected to a pressure source for the piston driving medium, for example via the line 38 and via a cock 39, to a line 40 of a drinking water supply net.

FIG. 3 shows the supply container 10 after discharging therefrom of the liquid sample into an analysis device 41. The drinking water which is used as a piston driving medium is fed via opening 19 into the sample container 10, piston 13 is moved to its lower end position and the initial position for a new sample test. After the sample container 10 has been emptied and removed from the plug-in coupling 37 it is subjected to cleaning. A cleaning liquid can be fed under pressure or vacuum into container 10 through the opening 16. Before connecting the sample container 10 to the plug-in coupling 20 again, piston 13 is moved by filling of water through the opening 19 of the sample container 10, to the initial position shown in FIG. 3.

After the coupling of the sample container 10 to the plug-in coupling 20 has taken place, piston 13 is also in its lower initial position, and the cylindrical chamber 15 of container 10 is filled with water. Before the beginning of the sample removal, the control medium, for example hydraulic oil or the like, is pressed via line 28 into the chamber 29 of the dosing pump cylinder 23 so that its piston 24 is moved against the force of the restoring spring 26 to the end position. Thereby the piston driving medium which is here water, positioned in the chamber occupied by the restoring spring 26, flows, via opening 22 and one-way valve 31 and line 30, into a collecting container 32. Finally if the multi-way valve 35 is switched over, and line 28 is, via this valve vented into the collecting container 33 for the control medium, piston 24 of the closing pump cylinder 23 is moved back by the force of the restoring spring 26, also damped by rearwardly flowing hydraulic oil in line 28, to its initial position defined by the movable stop or abutment 27. Thereby due to a slight built-up under pressure, the one-way valve 21 opens, and water contained in the chamber 15 of the sample container 10 is sucked via plug-in coupling 20 at opening 22 into the dosing pump cylinder 23. Thus the quantity of water precisely defined by dimensions of the pump cylinder and the stroke of the pump piston is sucked out from the chamber 15 of the sample container. Upon the removal of water, the freely movable piston 13 of the sample container is moved upwardly, and the liquid to be removed is sucked via opening 16 into the sample container 10. The entire sample removal process takes place relatively slowly and with a small underpressure so that the aforementioned volatilization of carbon hydrogens from the liquid would be avoided.

The device can be modified in many ways. For example, the pump piston 24 can, via the piston rod 25, be mechanically adjusted. The piston driving medium must not only be fed via line 30 into the collecting container 32 but also can be led to the atmosphere via the one-way valve 31.

It will be understood that each of the elements described above, or two or more together, may also find a useful application in other types of devices for removing liquid samples differing from the types described above.

While the invention has been illustrated and described as embodied in a device for removing liquid samples, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. In a device for the removal of liquid samples from natural or artificial liquid collecting or flow receptacles, comprising a cylinder sample container which simultaneously forms a sample transporting container, a piston freely movable in said container and subdividing said container into two cylindrical chambers, one of said chambers having a first opening for a liquid sample and provided with a check valve and another of said chambers having a second opening for a piston-driving medium, the improvement comprising: a leakage free coupling unit fluidly connected to said second opening for connection with the piston-driving medium and having means to close the coupling unit at two ends thereof; and a dosing device for the piston-driving medium, said dosing device being fluidly connected to said coupling unit and including a dosing pump cylinder receiving the piston-driving medium, a pump piston and a restoring spring, said pump piston being movable in said pump cylinder to a predetermined position against said spring.

2. The device as defined in claim 1, further including a storage container for the piston-driving medium; a first valve interconnected between said dosing pump cylinder and said plug-in coupling unit; and a second valve interconnected between said storage container and said dosing pump cylinder so said dosing pump cylinder receiving the piston-driving medium is connected to said plug-in coupling unit via said first valve and to said storage container via said second valve, said first and second valve being formed so as to prevent the piston-driving medium from flowing simultaneously in two opposite directions when said plug-in coupling unit is connected to said dosing device.

3. The device as defined in claim 1, wherein said sample container has an opening admitting a sample from a receptacle, said freely movable piston is formed so as to be tightly guided in said sample container up to said admitting opening to prevent air influence at an end discharge position thereof.

4. The device as defined in claim 3, wherein said pump piston is mechanically movable.

5. The device as defined in claim 3, wherein said dosing pump cylinder is hydraulically actuated; and further including a control medium pressure source (34) and a control valve (35) connected to said control medium pressure source, said dosing pump cylinder being connected to said pressure source by said control valve (35).

6. The device as defined in claim 5,
wherein said dosing device further include an adjustable stop (27), said pump piston being, under prestressing of said restoring spring, adjustable by said stop to an initial position thereof.

7. The device as defined in claim 6, wherein said control valve, said storage container and said pressure source are installed in an operation and control part, said sample container and said dosing device being separated from said operation and control part.

8. The device as defined in claim 7, wherein said sample container and said freely movable piston operating in contact with a liquid sample are made of a material which is inert to liquid to be sampled.

* * * * *